(12) United States Patent
LeCronier et al.

(10) Patent No.: US 9,050,149 B2
(45) Date of Patent: Jun. 9, 2015

(54) COMPRESSION TRANSMISSION COLLAR FOR FASTENING

(71) Applicants: David LeCronier, Oxford, MI (US); Patrick Atkinson, Grand Blanc, MI (US)

(72) Inventors: David LeCronier, Oxford, MI (US); Patrick Atkinson, Grand Blanc, MI (US)

(*) Notice: Subject to any disclaimer, the term of this patent is extended or adjusted under 35 U.S.C. 154(b) by 224 days.

(21) Appl. No.: 13/663,812

(22) Filed: Oct. 30, 2012

(65) Prior Publication Data

US 2014/0249529 A1   Sep. 4, 2014

Related U.S. Application Data

(63) Continuation of application No. 12/901,728, filed on Oct. 11, 2010, now Pat. No. 8,317,789.

(51) Int. Cl.
| | |
|---|---|
| *A61B 17/56* | (2006.01) |
| *A61B 17/72* | (2006.01) |
| *A61B 17/68* | (2006.01) |
| *A61B 17/86* | (2006.01) |

(52) U.S. Cl.
CPC ......... *A61B 17/7241* (2013.01); *A61B 17/7258* (2013.01); *A61B 17/7275* (2013.01); *A61B 17/686* (2013.01); *A61B 17/8695* (2013.01); *A61B 2017/564* (2013.01); *A61B 2017/681* (2013.01)

(58) Field of Classification Search
CPC ........... A61B 17/7233; A61B 17/7258; A61B 17/7275; A61B 17/7241
USPC ............................................................ 606/64
See application file for complete search history.

(56) References Cited

U.S. PATENT DOCUMENTS

| | | | | |
|---|---|---|---|---|
| 859,054 | A * | 7/1907 | Fischer .......................... | 411/145 |
| 7,195,633 | B2 * | 3/2007 | Medoff et al. ................. | 606/309 |
| 8,317,789 | B2 * | 11/2012 | LeCronier et al. .............. | 606/64 |
| 2004/0122428 | A1 * | 6/2004 | Johnstone ........................ | 606/62 |
| 2005/0154392 | A1 * | 7/2005 | Medoff et al. .................. | 606/69 |
| 2009/0018542 | A1 * | 1/2009 | Saravia et al. .................. | 606/63 |
| 2011/0313420 | A1 * | 12/2011 | LeCronier et al. .............. | 606/62 |

* cited by examiner

*Primary Examiner* — Ellen C Hammond
(74) *Attorney, Agent, or Firm* — Dickinson Wright, PLLC

(57) ABSTRACT

A compression transmission collar apparatus (20) for implantation into a bone (22) with a hole (28) having a hole wall (32) comprising an intramedullary nail (34) defining a bore (40) and a threaded fastener (42) and a compression transmission collar (58) including an exterior face (64) and a top edge (60) and a bottom edge (62) and a first end (70) intersecting the top edge (60) at an acute angle and the bottom edge (62) at an obtuse angle and a second end (72) intersecting the top edge (60) at an obtuse angle and the bottom edge (62) at an acute angle and the first end (70) partially overlapping and opposing the second end (72) to define a slit (74) such that applying a compressional load to the top edge (60) causes the first end (70) to slide relative to and along the second end (72) causing the compression transmission collar (58) to compress axially and expand radially pressing the exterior face (64) against the hole wall (32).

3 Claims, 7 Drawing Sheets

COMPRESSION TRANSMISSION COLLAR FOR FASTENING

CROSS REFERENCE TO RELATED APPLICATION

This application is a Continuation of U.S. application Ser. No. 12/901,728, filed Oct. 11, 2010, now U.S. Pat. No. 8,317,789, the entire contents of which is incorporated herein by reference in its entirety.

STATEMENT REGARDING FEDERALLY SPONSORED RESEARCH

This invention was made with Government support under contract numbers W81XWH0720119 and W81XWH1120128 awarded by the Unites States Army Medical Research Acquisition Activity. The Government has certain rights in this invention.

BACKGROUND OF THE INVENTION

1. Field of the Invention

The subject invention generally relates to a compression transmission collar apparatus for fastening two members. The subject invention is specifically applicable to a compression transmission collar apparatus that is implantable into bone for use in treating bone factures by skeletal fixation medical procedures.

2. Description of the Prior Art

Skeletal fixation is a well known type of medical procedure for treating bone factures. The skeletal fixation procedures known in the art typically call for the use of fasteners to fixate, or fasten, the ends of the fractured bone to one another. Accordingly, the fasteners and other related hardware used in typical skeletal fixation procedures are analogous to the fasteners and other related hardware used in other applications such as carpentry, construction, and assembly.

U.S. patent application Ser. No. 12/818,395 to LeCronier et al. teaches an easily implantable and stable nail-fastener apparatus for skeletal fixation including an intramedullary nail for insertion into the medullary canal of a bone. The intramedullary nail defines a threaded bore extending transverse to the intramedullary nail. A threaded fastener including a threaded portion extending transversely to the intramedullary nail threadedly engages the bore of the intramedullary nail. A compression transmission collar of annular shape having an exterior face and a top edge is provided for receiving a compressional load from the threaded fastener and transmitting the compressional load to the intramedullary nail. When simplified to the more general field of fasteners, the bone essentially comprises a first member defining a hole having a hole wall and the intramedullary nail comprises a second member defining a threaded bore. A threaded fastener then is provided to threadedly engage the bore and fixate the first member to the second member. Lastly, a compression transmission collar of annular shape is provided to transmit the compressional load of the fastener to at least one of the fastened members.

One compression transmission collar well known in the art of fasteners and related hardware is the helical lock washer. Expired U.S. Pat. No. 1,655,018 to Loutrel teaches a compression spring washer for use with fasteners. The Loutrel design discloses a helical shaped washer having a top edge and a bottom edge and a first end and a second end defining a slit. The top edge is designed to contact the threaded fastener for receiving a compressional load from the threaded fastener and the bottom edge is design to contact and transmit the compressional load to one of the fastened members. Finally, due to the helical shape of the Loutrel design, the compression spring washer has an extended length and a compressed length.

A problem with the compression transmission collars known in the art, such as the helical lock washer, is that the compressional load received by the compression transmission collar is transmitted axially to the surface of the fastened member surrounding the hole or the bore. Axial transmission of the compressional load in close proximity to the hole or bore is particularly problematic where at least one of the fastened members is a brittle or easily deformable material. In such cases, the axial transmission of the compressional load can easily cause the material to break, crack, or deform because it has already been weakened by the presence of the hole or bore. This problem is especially significant in skeletal fixation procedures because they involve the repair of an already fractured bone which is a brittle material. Accordingly, there remains a need for a compression transmission collar that provides for the fastening of two members but does not transmit a compressional load to one of the fastened members in the axial direction.

SUMMARY OF THE INVENTION

The subject invention provides for a compression transmission collar including an exterior face having an exterior diameter providing at least partial insertion of the compression transmission collar into the hole of the first member. The bottom edge of the compression transmission collar contacts the second member for transmitting the compressional load to the second member. The first end of the compression transmission collar intersects the top edge at an acute angle and the bottom edge at an obtuse angle. The second end of the compression transmission collar intersects the top edge at an obtuse angle and the bottom edge at an acute angle. Accordingly, the first end at least partially overlaps and opposes the second end to define the slit in the compression transmission collar. In response to the application of a compressional load to the top edge of the compression transmission collar, the first end slides relative to and along the second end causing the compression transmission collar to expand radially and compress axially between the extended length and the compressed length. The radial expansion of the compression transmission collar presses the exterior face of the compression transmission collar against the hole wall of the first member to securely fasten the first member to the threaded fastener and the second member.

By providing a compression transmission collar that expands in response to the application of a compressional load, the subject invention solves the problem associated with using fasteners that apply a compressional load in the axial direction in close proximity to a hole or bore in applications where at least one of the fastened members is of a brittle or easily deformable material. The expansion of the compression transmission collar allows for the fastening of the members without applying a compressional load to the first member and thereby avoids the risk of breaking, cracking, or deforming the first member. Accordingly, the subject invention is particularly useful in applications where at least the first member is of a brittle or easily deformable material such as glass, ceramic, rubber, polymers, and crystalline materials. Given the brittle characteristics of bone, the subject invention is especially useful in the field of skeletal fixation where preserving the integrity of the fastened members is vital for successful treatment of a fractured bone.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Figure 1:
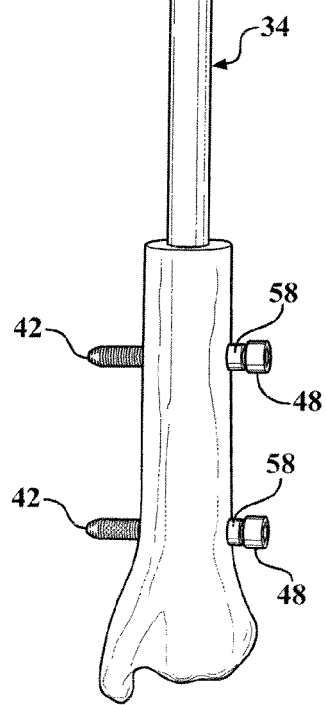
FIG. 1 is a side perspective view of the complete compression transmission collar apparatus implanted in the bone.

Referring to the Figures, wherein like numerals indicate corresponding parts throughout the several views, a compression transmission collar apparatus 20 is generally shown for implantation into a bone 22 during a skeletal fixation medical procedure. The bone 22 includes a medullary canal 24 surrounded by cortex 26. The bone 22 also includes a near cortex hole 28 and a far cortex hole 30 located in the cortex 26. The near cortex hole 28 has a near cortex hole diameter ($O_{NC}$) and a near cortex hole wall 32. The far cortex hole 30 has a far cortex hole diameter ($D_{FC}$). The near cortex hole 28 and the far cortex hole 30 are positioned on opposing sides of the medullary canal 24 with the near cortex hole diameter ($D_{NC}$) being greater than the far cortex hole diameter ($D_{FC}$) although the present invention is not limited to this configuration. It is envisioned that the compression transmission collar apparatus 20 of the present invention may be used in a configuration lacking a far cortex hole 30 altogether.

Figure 2:
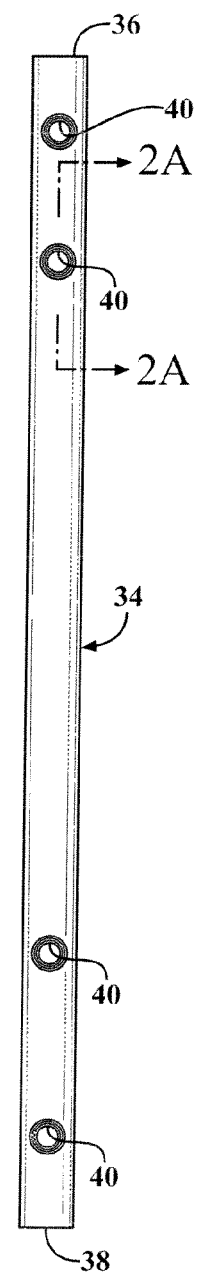
FIG. 2 is a front view of the intramedullary nail.
Figure 2A:
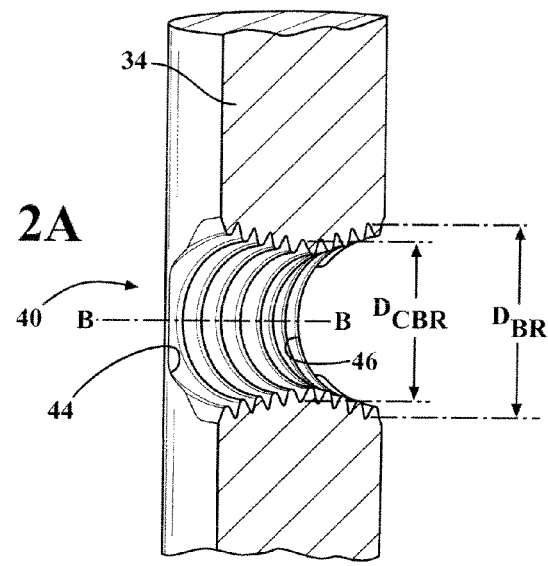
FIG. 2A is an enlarged perspective view taken along line 2A-2A of FIG. 2 illustrating the bore of the intramedullary nail.
Figure 3:
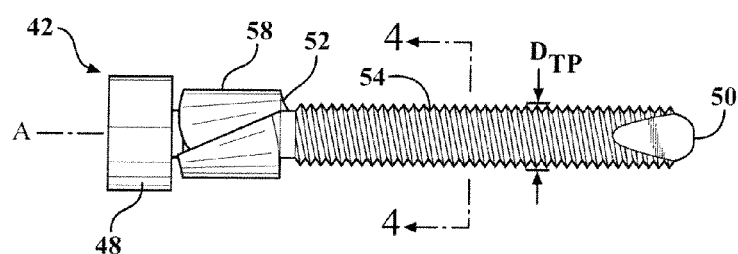
FIG. 3 is a side view of the threaded fastener and the compression transmission collar.
Figure 4:
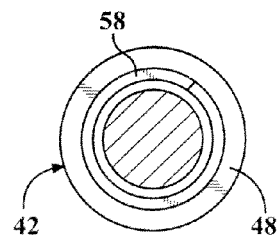
FIG. 4 is an enlarged cross-sectional view taken along line 4-4 of FIG. 3 illustrating the threaded fastener and the compression transmission collar.
Figure 5:
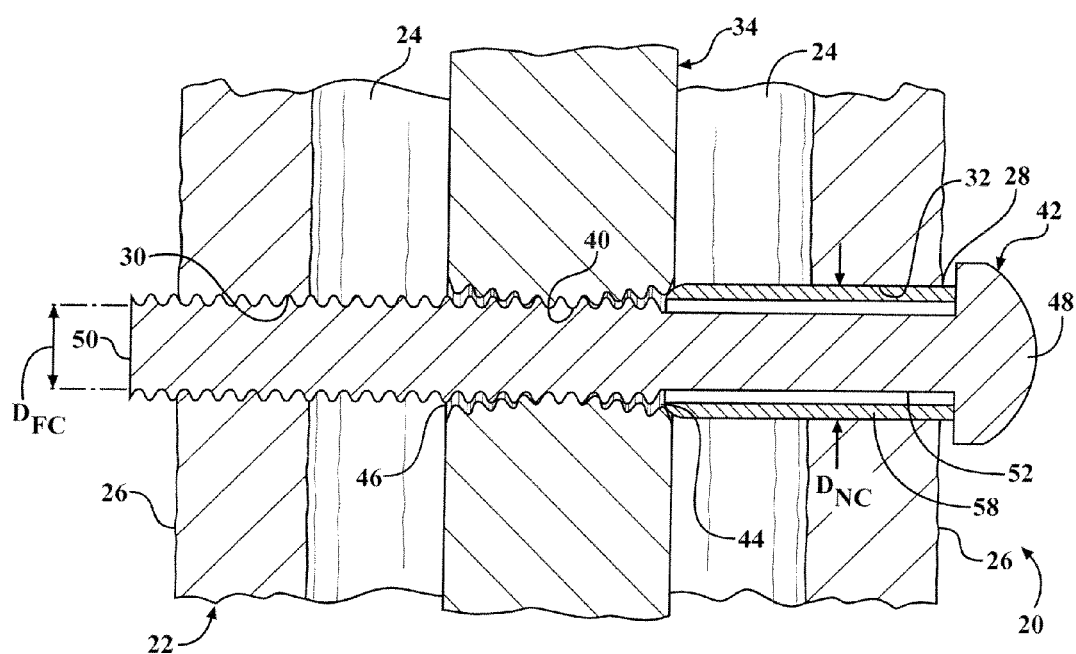
FIG. 5 is an enlarged horizontal fragmentary cross-sectional view of a portion of FIG. 1 illustrating the compression transmission collar apparatus wherein the threaded fastener is installed parallel to the bore axis.
Figure 6:
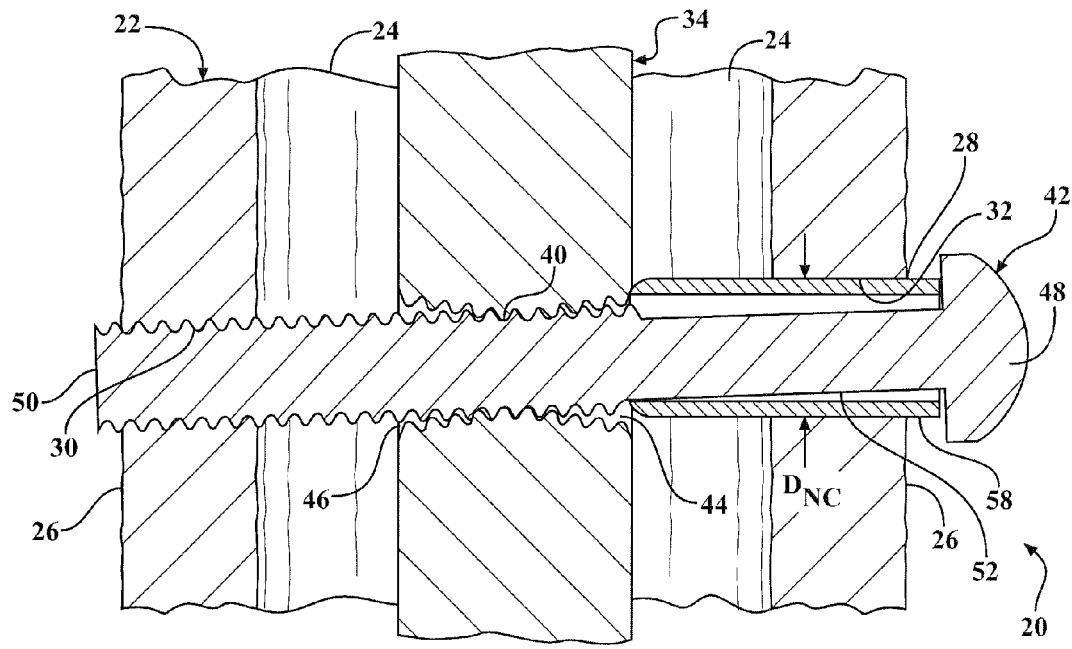
FIG. 6 is an enlarged horizontal fragmentary cross-sectional view of a portion of FIG. 1 illustrating the compression transmission collar apparatus wherein the threaded fastener is installed at an oblique angle relative to the bore axis.

The compression transmission collar apparatus 20 further includes an intramedullary nail 34 for insertion into the medullary canal 24 of the bone 22. The intramedullary nail 34 extends between a top end 36 and a bottom end 38. The intramedullary nail 34 defines a bore 40 extending transverse to the intramedullary nail 34 for receiving a threaded fastener 42. Accordingly, the bore 40 may extend at a right angle or an oblique angle to the intramedullary nail 34. The bore 40 is threaded and has a bore axis (B) extending between a near opening 44 and a far opening 46 transverse to the intramedullary nail 34. The bore 40 also has a bore diameter ($D_{BR}$) including a central bore diameter ($D_{CBR}$) equal in diameter to the far cortex hole diameter ($D_{FC}$). The central bore diameter ($D_{CBR}$) is disposed centrally between the near opening 44 and the far opening 46 of the bore 40. As shown in FIG. 2A, the bore diameter ($D_{BR}$) increases from the central bore diameter ($D_{CBR}$) to the near opening 44 and from the central bore diameter ($D_{CBR}$) to the far opening 46. Accordingly, the bore 40 defined by the intramedullary nail 34 has a hyerboloid shape although a traditional cylindrically shaped bore 40 could alternatively be used. However, as shown in FIG. 6, the hyerboloid shape of the bore 40 is advantageous because it allows the threaded fastener 42 to be mounted at a variety of angles in relation to the bore axis (B). This advantage is especially important during skeletal fixation medical procedures because doctors often do not have the ability or time to assure perpendicular mounting.

The threaded fastener 42 extends along a fastener axis (A) between a head 48 and an end 50. The threaded fastener 42 further includes a compression portion 52 and a threaded portion 54 and an unthreaded portion 56 adjacent to the end 50. The compression portion 52 does not engage the threads of the bore 40 and so the compression portion 52 may be threaded or unthreaded. The compression portion 52 has a compression portion diameter ($D_{CP}$) that is smaller than or equal to the threaded portion diameter ($D_{TP}$). The threaded portion 54 has a threaded portion diameter ($D_{TP}$) that is equal the central bore diameter ($D_{CBR}$). Where the configuration includes a far cortex hole 30, the far cortex hole diameter ($D_{FC}$) may be equal to the central bore diameter ($D_{CBR}$) and the threaded portion diameter ($D_{TP}$). The use of a threaded fastener 42 including only a threaded portion 54 running from the head 48 to the end 50 is also contemplated by the present invention. The threaded fastener 42 extends through the intramedullary nail 34 and the far cortex hole 30 so as to extend transversely to the intramedullary nail 34 for threadedly engaging the bore 40. In a configuration absent the far cortex hole 30, the fastener extends only through the intramedullary nail 34. By threadedly engaging the bore 40, the threaded fastener 42 applies a compressional load to the intramedullary nail 34 and fixates the intramedullary nail 34 within the medullary canal 24 of the bone 22.

The compression transmission collar apparatus 20 further includes a compression transmission collar 58 of annular shape having a top edge 60 and a bottom edge 62. The top edge 60 contacts the head 48 of the threaded fastener 42 for receiving the compressional load from the threaded fastener 42. The bottom edge 62 contacts the intramedullary nail 34 for transmitting the compressional load to the intramedullary nail 34. The compression transmission collar 58 also has an exterior face 64 having an exterior diameter ($D_E$) and an interior face 66 having an interior diameter ($D_I$). The an interior diameter ($D_I$) is greater than the compression portion diameter ($D_{CP}$) of the fastener. The interior face 66 of the compression transmission collar 58 defines an interior space 68 for providing space at least partially about the threaded fastener 42 for allowing the fastener axis (A) to be variously disposed relative to the interior space 68. Accordingly, the compression transmission collar 58 transmits the compressional load of the threaded fastener 42 to the intramedullary nail 34 during fixation.

Figure 11A:
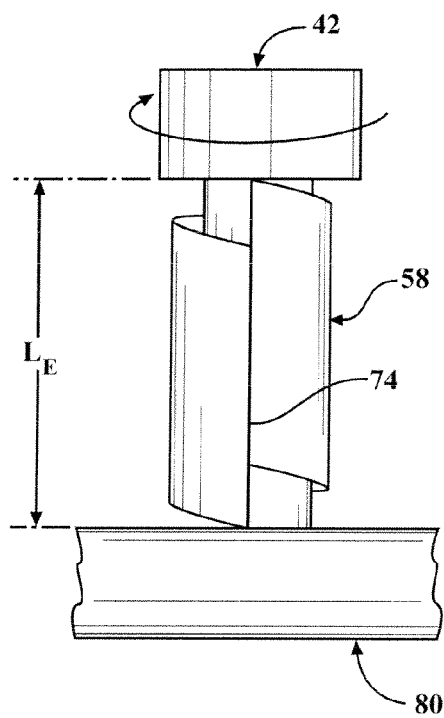
FIG. 11A is a side view of the threaded fastener, a portion of the second member, and the compression transmission collar in an axially extended state wherein the threaded fastener is installed at a perpendicular angle to the second member.
Figure 11B:
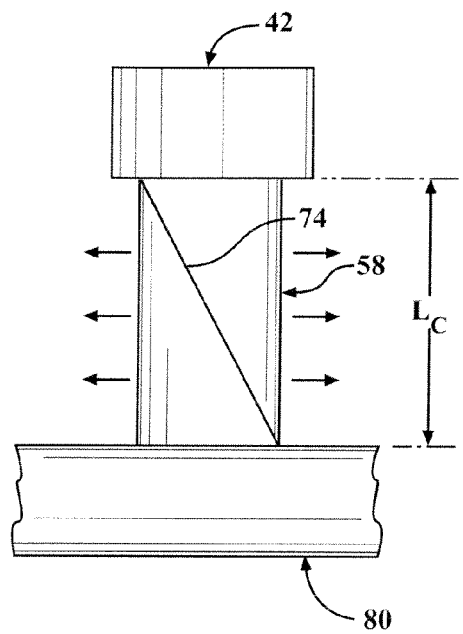
FIG. 11B is a side view of the threaded fastener, a portion of the second member, and the compression transmission collar in an axially compressed state wherein the threaded fastener is installed at a perpendicular angle to the second member and the radial expansion of the compression transmission collar is shown.
Figure 12:
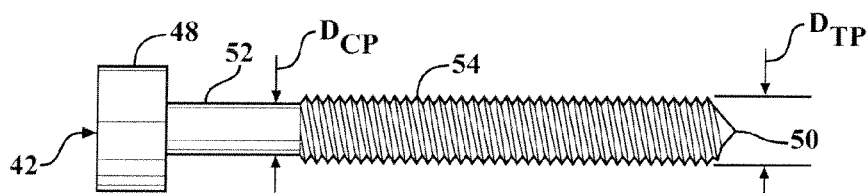
FIG. 12 is a side view of a threaded fastener including a threaded portion adjacent a compression portion being unthreaded.
Figure 13:
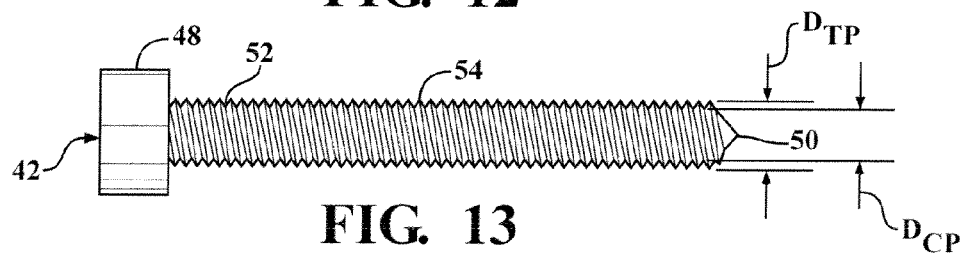
FIG. 13 is a side view of a threaded fastener including a threaded portion adjacent a compression portion being threaded.
Figure 14:
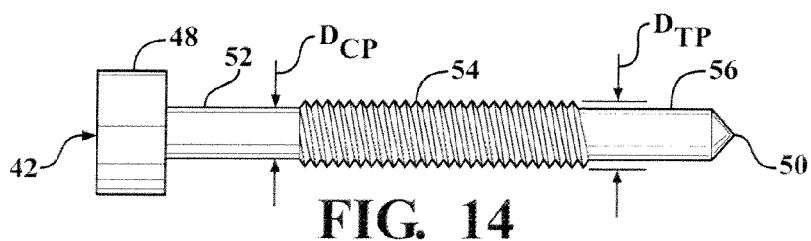
FIG. 14 is a side view of a threaded fastener including a threaded portion disposed between a compression portion being unthreaded and an unthreaded portion adjacent the end.

The compression transmission collar 58 has an extended length ($L_E$) and a compressed length ($L_C$). As shown in FIG. 11A, the extended length ($L_E$) equals the distance between the top edge 60 and the bottom edge 62 of the compression transmission collar 58 before the compressional force has been applied or after the compressional force has been removed. As shown in FIG. 11B, the compressed length ($L_C$) equals the final or steady state distance between the top edge 60 and the bottom edge 62 of the compression transmission collar 58 after the compressional force has been applied but before the compressional force has been removed.

Figure 8A:
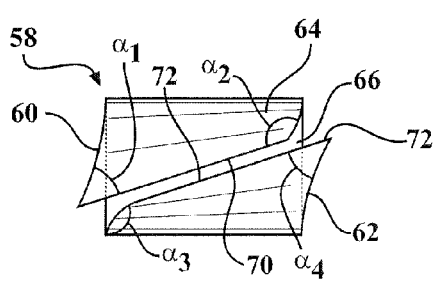
FIG. 8A is a side view of a second embodiment of the compression transmission collar wherein the slit is further defined by a gap having a gap distance greater then zero.
Figure 8B:
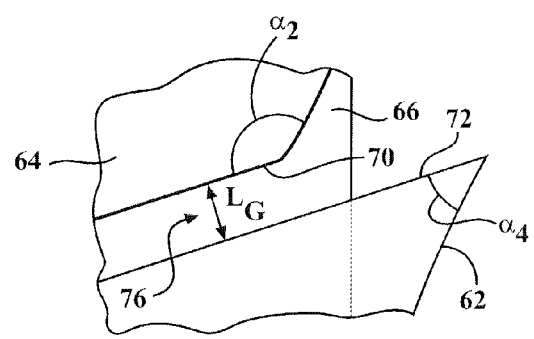
FIG. 8B is an enlarged fragmentary view of a portion of FIG. 8A illustrating the gap of the compression transmission collar.
Figure 9A:
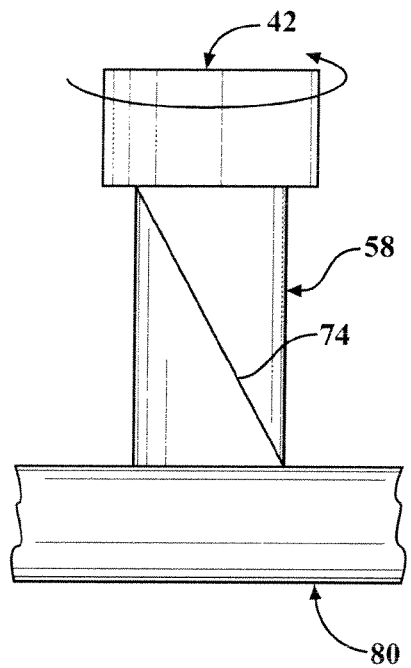
FIG. 9A is a side view of the threaded fastener, a portion of the second member, and the compression transmission collar in an axially compressed state.
Figure 9B:
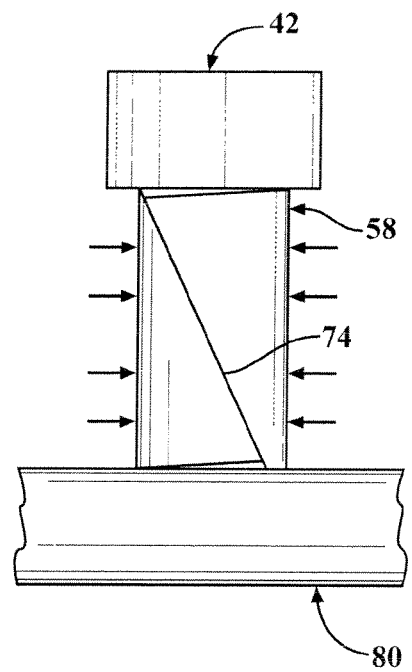
FIG. 9B is a side view of the threaded fastener, a portion of the second member, and the compression transmission collar in an axially extended state wherein the radial contraction of the compression transmission collar is shown.
Figure 10A:
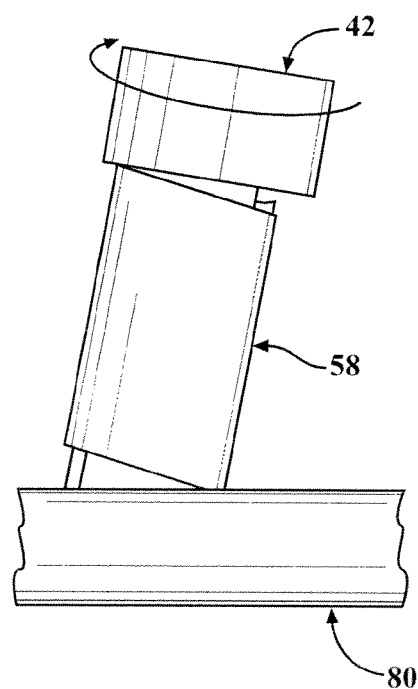
FIG. 10A is a side view of the threaded fastener, a portion of the second member, and the compression transmission collar in an axially extended state wherein the threaded fastener is installed at an oblique angle to the second member.
Figure 10B:
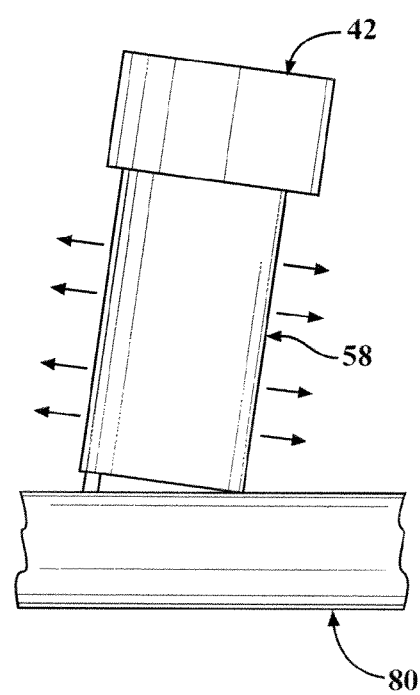
FIG. 10B is a side view of the threaded fastener, a portion of the second member, and the compression transmission collar in an axially compressed state wherein the threaded fastener is installed at an oblique angle to the second member and the radial expansion of the compression transmission collar is shown.

The compression transmission collar 58 further includes a first end 70 and a second end 72. As shown in FIGS. 8A and 8B, the first end 70 intersects the top edge 60 at an acute angle $\alpha_1$ and the bottom edge 62 at an obtuse angle $\alpha_2$. The second end 72 intersects the top edge 60 at an obtuse angle $\alpha_3$ and the bottom edge 62 at an acute angle $\alpha_4$. The first end 70 partially overlaps and opposes the second end 72 to define a slit 74 such that applying the compressional load to the top edge 60 causes the first end 70 to slide relative to and along the second end 72. Accordingly, the application of the compressional load to the top edge 60 of the compression transmission collar 58 causes the compression transmission collar 58 to compress axially between the extended length ($L_E$) and the compressed length ($L_C$). The axial compression of the compression transmission collar 58 corresponds to a radial expansion of the compression transmission collar 58. In other words, as the compression transmission collar 58 is axially compressed, the circumference of the compression transmission collar 58 increases. Thus, the exterior face 64 of the compression transmission collar 58 is pressed against the near cortex hole wall 32 in response to the radial expansion of the compression transmission collar 58 caused by the application of the compressional load. The pressure exerted by the exterior face 64 of the compression transmission collar 58 against the near cortex hole wall 32 fastens the threaded fastener 42 and the intramedullary nail 34 to the bone 22 and prevents movement of the compression transmission collar 58 relative to the near cortex hole 28.

The compression transmission collar 58 is made of a resilient material so that the compression transmission collar 58 expands axially and contracts radially in response to removal of the compressional load. The resilient material may be but is not limited to a metal, a metal alloy, a rubber, or a polymer. Obviously, other materials may be employed and their use is envisioned by the present invention.

Figure 7A:
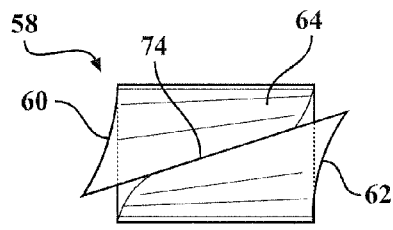
FIG. 7A is a side view of a first embodiment of the compression transmission collar wherein the slit is further defined by a gap having a gap distance equal to zero.
Figure 7B:
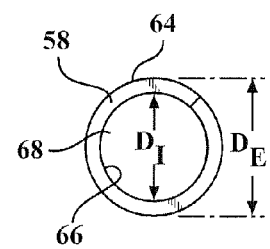
FIG. 7B is an end view of the compression transmission collar of FIG. 7A.

As shown in FIGS. 7A and 8A, in one embodiment of the present invention, the compression transmission collar 58 extends in a helical path between the first end 70 and the second end 72 when the compression transmission collar 58 is at the extended length ($L_E$). The present invention is not limited to this embodiment as the use of a compression transmission collar 58 that does not extend in a helical path between the first end 70 and the second end 72 is also envisioned. Also shown in FIGS. 7A and 8A, the exterior face 64 of the compression transmission collar 58 is generally trapezoidal in shape. The present invention alternatively envisions use of a compression transmission collar 58 including an exterior face 64 having a non-trapezoidal shape.

The slit 74 in the compression transmission collar 58 is further defined by a gap 76 having a gap distance ($L_G$). The gap distance ($L_G$) equals the tangential distance between the first end 70 and the second end 72. In one embodiment of the present invention, as shown in FIG. 8A, the gap distance ($L_G$) is greater than zero when the compression transmission collar 58 is at the extended length ($L_E$). In this embodiment, the first end 70 and the second end 72 close the gap 76 such that the gap distance ($L_G$) becomes equal to zero in response to the application of the compressional load to the top edge 60 of the compression transmission collar 58. Thus, in this embodiment, the first end 70 is spaced from the second end 72 by the gap 76 before the application of the compressional force and after the removal of the compressional force. In another embodiment of the present invention, as shown in FIG. 7A, the slit 74 is further defined by a gap 76 having a gap distance ($L_G$) equal to zero. In this embodiment, the first end 70 and the second end 72 remain in contact with one another before, during, and after the application of the compressional load.

The present invention also includes a method of skeletal fixation wherein the intramedullary nail 34 is fastened to the bone 22. The method proceeds with the step of creating a bore 40 including threads in the intramedullary nail 34 extending transverse to the intramedullary nail 34 and inserting the intramedullary nail 34 into the medullary canal 24 of the bone 22. The method further includes the steps of forming the near cortex hole 28 in the cortex 26 of the bone 22 in radially overlapping relationship to the bore 40 of the intramedullary nail 34 and similarly forming the far cortex hole 30 in the cortex 26 of the bone 22 in radially overlapping relationship to the bore 40 of the intramedullary nail 34. The method also includes the steps of inserting the compression transmission collar 58 into the near cortex hole 28 and inserting the threaded fastener 42 through the compression transmission collar 58 and into the bore 40 of the intramedullary nail 34. The method additionally includes the steps of applying torque to the head 48 of the threaded fastener 42 for threadedly engaging and advancing the threaded fastener 42 through the bore 40 of the intramedullary nail 34 and the far cortex hole 30 for applying compressional load to the top edge 60 of the compression transmission collar 58 to compress the compression transmission collar 58 axially between the extended length ($L_E$) and the compressed length ($L_C$). The axial compression is accomplished by sliding the first end 70 of the compression transmission collar 58 relative to and along the second end 72 of the compression transmission collar 58 and results in the radial expansion of the compression transmission collar 58 within the near cortex hole 28. The method proceeds with the step of removing torque from the head 48 of the threaded fastener 42 in response to compressing the compression transmission collar 58 to the compressed length ($L_C$). A hard stop is felt by the operator in response to the compression transmission collar 58 reaching the compressed length ($L_C$) to notify the operator to remove the torque from the head 48 of the threaded fastener 42. The hard stop feature thus helps prevent the undertightening or overtightening of the threaded fastener 42. This feature is especially advantageous during skeletal fixation medical procedures where time is limited and improper tightening cannot be easily corrected later because it quickly and positively notifies the doctor that he or she has properly installed and tightened the threaded fastener 42.

Figure 15A:
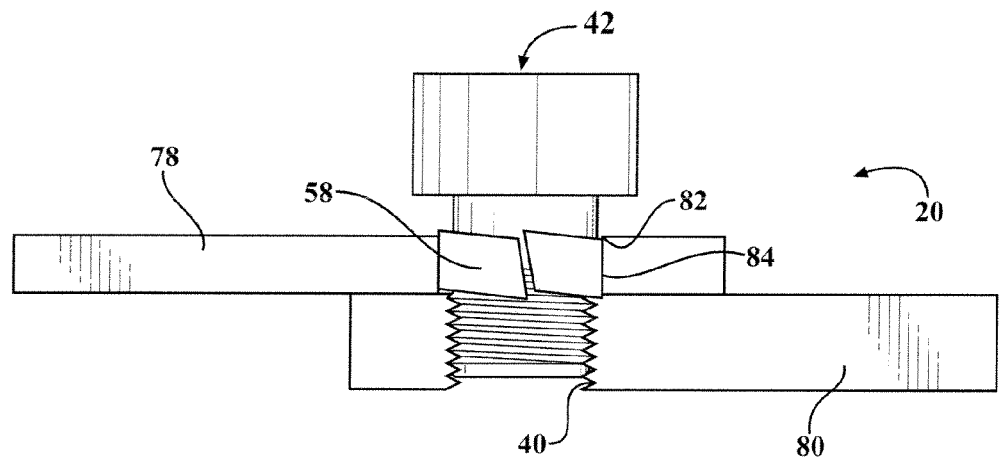
FIG. 15A is a side view looking transparently through the first member and the second member showing the installation of the threaded fastener and the compression transmission collar wherein the threaded fastener is engaging the bore of the second member and the compression transmission member is still in an axially extended state.
Figure 15B:
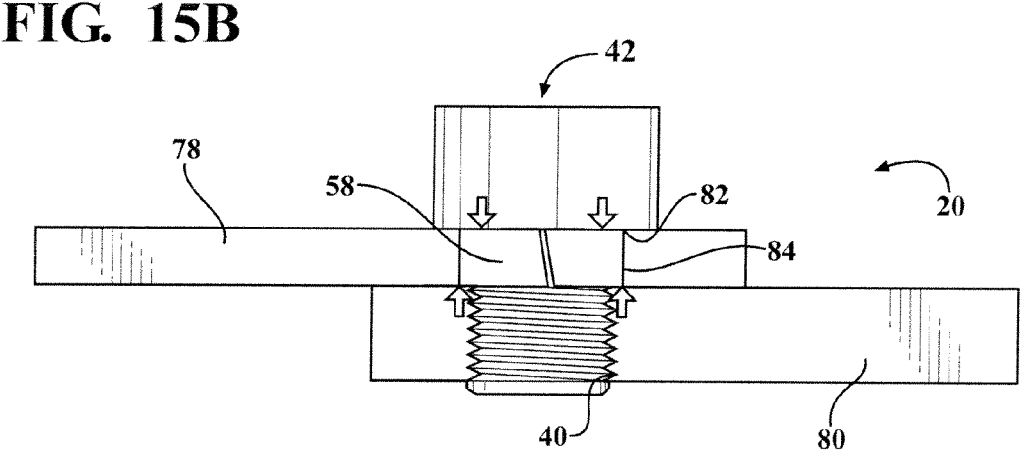
FIG. 15B is a side view looking transparently through the first member and the second member showing the installation of the threaded fastener and the compression transmission collar wherein the threaded fastener is applying a compressional load to the top edge of the compression transmission collar and the compression transmission collar is compressing axially and expanding radially.
Figure 15C:
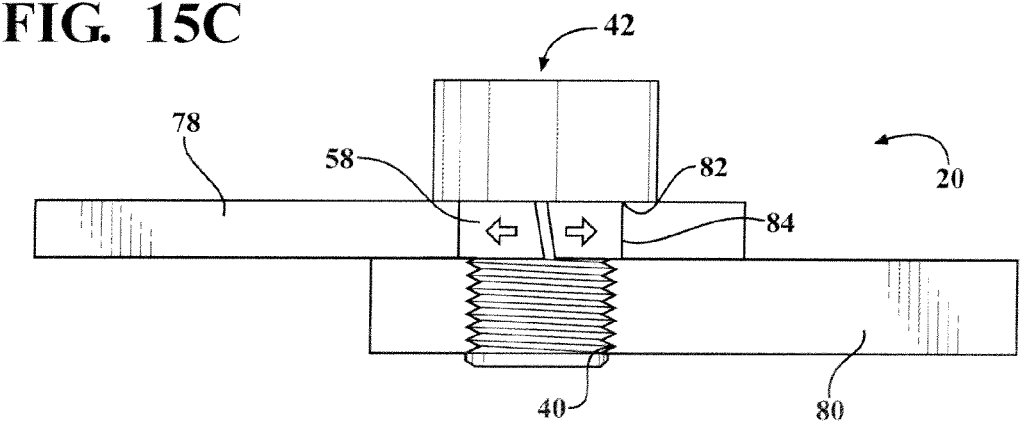
FIG. 15C is a side view looking transparently through the first member and the second member showing the installation of the threaded fastener and the compression transmission collar wherein the compression transmission collar is in an axially compressed state and has expanded radially so that the exterior face of the compression transmission collar is pressed against the hole wall of the first member.

The present invention also more generally relates to fastening structures for use outside of a skeletal fixation medical procedure. A compression transmission collar apparatus 20 for fastening two members 78, 80 is shown generally in FIGS. 15A-C. The compression transmission collar apparatus 20 includes a first member 78 defining a hole 82 having a hole wall 84 and a second member 80 defining a bore 40 that is threaded. The compression transmission collar apparatus 20 further includes a compression transmission collar 58 of annular shape and a threaded fastener 42 having a threaded portion 54 for threadedly engaging the bore 40. The compression transmission collar 58 has a top edge 60, a bottom edge 62, and an exterior face 64. The top edge 60 contacts the threaded fastener 42 for receiving a compressional load from the threaded fastener 42. The compression transmission collar 58 has an extended length ($L_E$) and a compressed length ($L_C$). The extended length ($L_E$) equals the distance between the top edge 60 and the bottom edge 62 of the compression transmission collar 58 before the compressional force has been applied or after the compressional force has been removed. The compressed length ($L_C$) equals the final or steady state distance between the top edge 60 and the bottom edge 62 of the compression transmission collar 58 after the compressional force has been applied but before the compressional force has been removed. The compression transmission collar 58 further includes and a first end 70 and a second end 72 defining a slit 74.

The exterior face 64 has an exterior diameter ($D_E$) providing at least partial insertion of the compression transmission collar 58 into the hole 82 of the first member 78. This allows the bottom edge 62 to contact the second member 80 for transmitting the compressional load to the second member 80. As shown in FIGS. 8A and 8B, the first end 70 intersects the top edge 60 at an acute angle $\alpha_1$ and the bottom edge 62 at an obtuse angle $\alpha_2$. The second end 72 intersects the top edge 60 at an obtuse angle $\alpha_3$ and the bottom edge 62 at an acute angle $\alpha_4$. The first end 70 at least partially overlaps and opposes the second end 72 to define the slit 74 such that applying the compressional load to the top edge 60 causes the first end 70 to slide relative to and along the second end 72. Accordingly, the application of the compressional load to the top edge 60 of the compression transmission collar 58 causes the compression transmission collar 58 to compress axially between the extended length ($L_E$) and the compressed length ($L_C$). The axial compression of the compression transmission collar 58 corresponds to a radial expansion of the compression transmission collar 58. In other words, as the compression transmission collar 58 is axially compressed, the circumference of the compression transmission collar 58 increases. Thus, the exterior face 64 of the compression transmission collar 58 is pressed against the hole wall 84 of the first member 78 in response to the radial expansion of the compression transmission collar 58 caused by the application of the compressional load. The pressure exerted by the exterior face 64 of the compression transmission collar 58 against the hole wall 84 acts to fasten the threaded fastener 42 and the second member 80 to the first member 78 and prevents movement of the compression transmission collar 58 relative to the hole 82 in the first member 78.

Obviously, many modifications and variations of the present invention are possible in light of the above teachings and may be practiced otherwise than as specifically described while within the scope of the appended claims.

What is claimed is:

1. A method of skeletal fixation of an intramedullary nail to a bone including a medullary canal surrounded by cortex and a near cortex hole and a far cortex hole by a threaded fastener having a head and a threaded portion and a compression transmission collar of resilient material and helical shape having a top edge and a bottom edge and a first end and a second end and an extended length and a compressed length and said first end intersecting said top edge at an acute angle and said bottom edge at an obtuse angle and said second end intersecting said top edge at an obtuse angle and said bottom edge at an acute angle and said first end partially overlapping and opposing said second end to define a slit, said method comprising the steps of;

creating a bore in the intramedullary nail extending transverse to the intramedullary nail including threads, inserting the intramedullary nail into the medullary canal of the bone, forming the near cortex hole in the cortex of the bone in radially overlapping relationship to the bore of the intramedullary nail, forming the far cortex hole in the cortex of the bone in radially overlapping relationship to the bore of the intramedullary nail, inserting the compression transmission collar into the near cortex hole, inserting the threaded fastener through the compression transmission collar and into the bore of the intramedullary nail, applying torque to the head of the threaded fastener for threadedly engaging and advancing the threaded fastener through the bore of the intramedullary nail and the far cortex hole and applying compressional load to the top edge of the compression transmission collar compressing the compression transmission collar axially between the extended length and the compressed length by sliding the first end of the compression transmission collar relative to and along the second end of the compression transmission collar and expanding the compression transmission collar radially within the near cortex hole in response to compressing the compression transmission collar axially, and removing torque from the head of the threaded fastener in response to compressing the compression transmission collar to the compressed length.

2. A method of skeletal fixation of an intramedullary nail to a bone including a medullary canal surrounded by cortex and a cortex hole by a fastener having a head and a compression transmission collar of resilient material having a top edge and a bottom edge and a first end and a second end and an extended length and a compressed length and said first end intersecting said top edge at an acute angle and said bottom edge at an obtuse angle and said second end intersecting said top edge at an obtuse angle and said bottom edge at an acute angle and said first end partially overlapping and opposing said second end to define a slit, said method comprising the steps of;

creating a bore in the intramedullary nail extending transverse to the intramedullary nail, inserting the intramedullary nail into the medullary canal of the bone, forming the cortex hole in the cortex of the bone in radially overlapping relationship to the bore of the intramedullary nail, inserting the compression transmission collar into the cortex hole, inserting the fastener through the compression transmission collar and into the bore of the intramedullary nail, applying torque to the head of the fastener for engaging and advancing the fastener through the bore of the intramedullary nail and applying compressional load to the top edge of the compression transmission collar compressing the compression transmission collar axially between the extended length and the compressed length by sliding the first end of the compression transmission collar relative to and along the second end of the compression transmission collar and expanding the compression transmission collar radially within the cortex hole in response to compressing the compression transmission collar axially, and removing torque from the head of the fastener in response to compressing the compression transmission collar to the compressed length.

3. A method of fixing an intramedullary nail to a bone including a medullary canal surrounded by cortex with a cortex hole using a fastener and a compression transmission collar, the compression transmission collar being formed of resilient material and having a top edge and a bottom edge presenting an extended length and a compressed length therebetween and a first end and a second end defining a slit therebetween, said method comprising the steps of;

providing the intramedullary nail with a bore;

inserting the intramedullary nail into the medullary canal of the bone so that the bore of the intramedullary nail is in radially overlapping relationship with the cortex hole of the bone;

inserting the compression transmission collar into the cortex hole, inserting the fastener through the compression transmission collar and into the bore of the intramedullary nail, applying torque to the fastener to advance the fastener through the bore of the intramedullary nail;

applying compressional load to the top edge of the compression transmission collar to compress the compression transmission collar axially from the extended length to the compressed length by sliding the first end of the compression transmission collar relative to and along the second end of the compression transmission collar;

removing torque from the fastener in response to compressing the compression transmission collar to the compressed length; and expanding the compression transmission collar radially within the cortex hole.

* * * * *